(12) United States Patent
Barcay et al.

(10) Patent No.: US 7,192,600 B2
(45) Date of Patent: Mar. 20, 2007

(54) PROCESS FOR USING WATER-SENSITIVE INSECTICIDES AS AN ACTIVE INGREDIENT IN A WATER-BASED PEST BAIT

(75) Inventors: S. John Barcay, Burnsville, MN (US); Douglas G. Anderson, Lakeville, MN (US); Thomas D. Nelson, Maplewood, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 10/115,459

(22) Filed: Apr. 2, 2002

(65) Prior Publication Data

US 2002/0155142 A1 Oct. 24, 2002

Related U.S. Application Data

(62) Division of application No. 09/870,098, filed on May 30, 2001, now Pat. No. 6,564,502, which is a division of application No. 09/404,985, filed on Sep. 22, 1999, now abandoned.

(51) Int. Cl.
*A01N 25/04* (2006.01)

(52) U.S. Cl. .................. 424/405; 424/84; 424/406; 424/409; 424/410; 514/120; 514/137

(58) Field of Classification Search ................ 424/405, 424/407, 409, 410, 84, 485, 659; 514/137
See application file for complete search history.

(56) References Cited

U.S. PATENT DOCUMENTS

| 4,168,591 | A | 9/1979 | Shaw |
| 4,514,960 | A | 5/1985 | Sears |
| 4,834,977 | A | 5/1989 | Kohama et al. |
| 4,845,103 | A | 7/1989 | Spaulding et al. |
| 4,945,107 | A | 7/1990 | Minetti |
| 4,985,413 | A | 1/1991 | Kohama et al. |
| 4,988,511 | A | 1/1991 | Demetre |
| 4,990,514 | A | 2/1991 | Bruey |
| 5,021,237 | A | 6/1991 | Bruey |
| 5,126,139 | A | 6/1992 | Geary |
| 5,152,096 | A | 10/1992 | Rudolph |
| 5,300,293 | A | 4/1994 | Minagawa et al. |
| 5,464,613 | A | 11/1995 | Barcay et al. |

(Continued)

FOREIGN PATENT DOCUMENTS

CH 374505 1/1964

(Continued)

OTHER PUBLICATIONS

Abstract, "Insect Killing Paste", *Shanghai Inst. of Entomology*, 1 pg. (Aug. 1997).

(Continued)

*Primary Examiner*—Neil S. Levy
(74) *Attorney, Agent, or Firm*—Merchant & Gould, P.C.

(57) ABSTRACT

A method of preparing a rapid acting bait composition which is water based and contains a water-sensitive insecticide as an active ingredient is described. The composition is easily applied into cracks and crevices and voids or other pest harborage areas to rapidly kill insect pests, particularly cockroaches. A kit is also described for preparation of the composition.

11 Claims, 1 Drawing Sheet

U.S. PATENT DOCUMENTS

| | | |
|---|---|---|
| 5,484,587 A | 1/1996 | Branly et al. |
| 5,547,955 A | 8/1996 | Silverman et al. |
| 5,607,682 A | 3/1997 | Wolfe et al. |
| 5,676,961 A | 10/1997 | Wolfe et al. |
| 5,820,855 A | 10/1998 | Barcay et al. |
| 5,850,707 A | 12/1998 | Fell et al. |
| 5,906,983 A | 5/1999 | Silverman et al. |
| 5,925,670 A | 7/1999 | Silverman et al. |
| 5,928,634 A | 7/1999 | Uick et al. |
| 5,953,854 A | 9/1999 | Hyatt |
| 5,968,540 A | 10/1999 | Brenner et al. |
| 5,983,557 A | 11/1999 | Perich et al. |
| 6,162,825 A | 12/2000 | Silverman et al. |
| 6,216,384 B1 | 4/2001 | Dickson et al. |
| 6,335,026 B1 * | 1/2002 | Katayama et al. .......... 424/409 |

FOREIGN PATENT DOCUMENTS

| | | |
|---|---|---|
| CN | 1155978 A | 8/1996 |
| EP | 05587061 B1 | 9/1993 |
| FR | 2 309 145 A | 11/1976 |
| GB | 2 190 839 A | 12/1987 |
| GB | 2 306 886 A | 5/1997 |
| WO | WO 91/07972 | 6/1991 |
| WO | WO 93/05651 | 4/1993 |
| WO | WO 95/24124 | 9/1995 |

OTHER PUBLICATIONS

Appel, A. G., "Performance of Gel and Paste Bait Products for German Cockroach (Dictyoptera: Blattellidae) Control: Laboratory and Field Studies," *Entomological Society of America*, vol. 85, No. 4, 10 pgs. (1992).

Reierson, D. A. et al., "Baits and Bait Technology," *Proceedings of the National Conference on Urban Entomology*, pp. 77-91 (1992).

Rust, M. K., "Managing Household Pests," *Advances in Urban Pest Management*, pp. 335-368 (1986).

Material Safety Data Sheet, "MAXFORCE," 1 pg. (1963).

\* cited by examiner

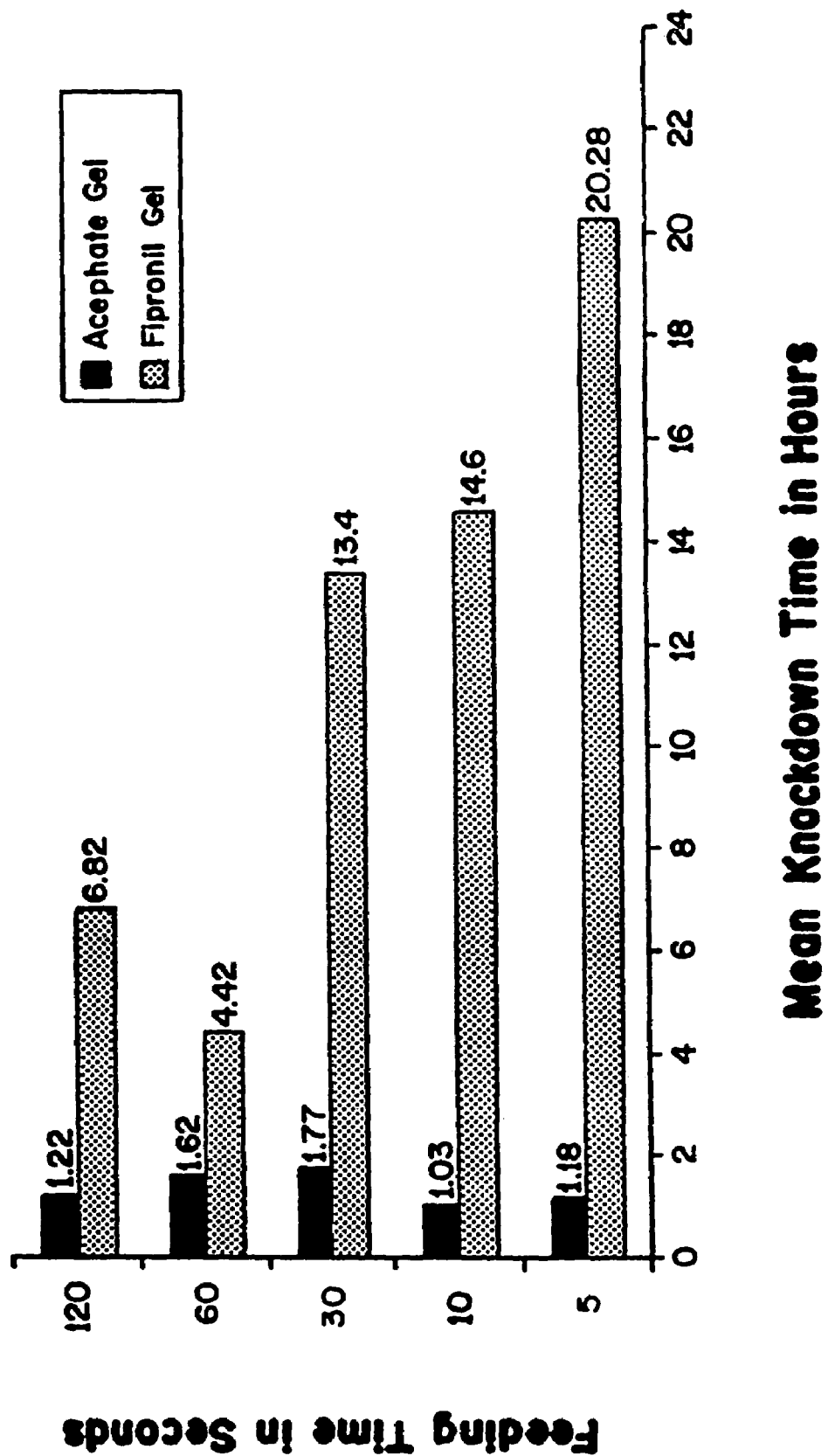

PROCESS FOR USING WATER-SENSITIVE INSECTICIDES AS AN ACTIVE INGREDIENT IN A WATER-BASED PEST BAIT

This application is a divisional of application Ser. No. 09/870,098, filed May 30, 2001, now U.S. Pat. No. 6,564,502 which is a divisional of application Ser. No. 09/404,985, filed Sep. 22, 1999 which application(s) are incorporated herein by reference.

FIELD OF THE INVENTION

This invention relates to a water-based, fast-acting pest bait containing a water-sensitive insecticide as the active ingredient for controlling insects, particularly cockroaches.

BACKGROUND OF THE INVENTION

Historically, toxic baits for controlling crawling insects such as cockroaches have been water-based. With cockroaches especially, water is presumed necessary for good bait performance. Unfortunately, water-based bait products rapidly lose effectiveness due to water loss, rancidity, breakdown of active ingredients and other factors. Studies of water-based paste baits have confirmed that water loss, repellent properties of active ingredients, and insecticide resistance are the most important factors affecting bait performance. Appel, A. G., *J. Econ Entomol.* 85 (4): 1176–1183 (1992), Robinson, W. H., *Proceedings of the National Conference on Urban Entomology* 77–91 (1992), and Rust, N. K., "Managing Household Pests", in *Advances in Urban Pest Management*, G. W. Bennett and M. Owens (eds), Van Norstrand Reinhold, N.Y. 335–368 (1986).

One approach to improve on water-based insecticide products has been to use a dust or a paste composition which includes a so-called water powder with the insecticide. This water powder is water encapsulated with hydrogenated soybean oil. Such a product is described in U.S. Pat. No. 5,820,855. Unfortunately, dust compositions have disadvantages such as drifting of the material when applied.

Water-free fat-based pest bait products are described in U.S. Pat. Nos. 5,464,613 and 5,464,613. These compositions are paste forms and include as a major ingredient a fat-based carrier. Although paste products do not drift, they are difficult to apply and require an applicator in applying pastes in cracks and crevices or into voids. Another disadvantage of the paste, water-free products are that they are not as fast-acting as water-based products, especially against cockroaches.

Acephate is a very desirable insecticide, particularly in killing cockroaches. Acephate's desirability is based on the fact that there is no known insecticide resistance and because it has a very low mammalian toxicity. However, acephate is not stable in water-based matrices over time. Although acephate has been described in the above water-free, fat-based patents, it is not currently used as an active ingredient in any commercially available cockroach bait. There is thus a need for improved rapid acting, water-based baits that utilize water-sensitive insecticides.

SUMMARY OF THE INVENTION

We have found in the present invention a method which allows a water-sensitive insecticide, for example, acephate, to be used successfully in a water-based matrix. The invention is a composition which, if desired, can be prepared at the site of application and applied to cracks, crevices and voids. The composition is active when formulated and, when applied, results in rapid kill of insect pests, particularly cockroaches. A preferred rapid acting composition is in the form of a gel.

Accordingly, the invention in its first aspect is a process for preparing a ready-to-use insecticidal bait composition including the steps of (a) dissolving a water sensitive insecticide in a specified amount of water, (b) combining the resulting insecticidal solution with a bait base containing a mixture of feeding stimulants and optionally containing one or more gelling agent(s), (c) agitating the resulting combination until thoroughly mixed, and, if desired, (d) allowing the mixed combination to form a gel or paste.

The present invention in a second aspect provides a ready-to-use insecticidal bait composition having a viscosity between about 50,000 to about 1,500,000 centipoise including (a) about 0.1 to 5.0 wt-% of a water-sensitive insecticide, (b) about 3 to 40 wt-% water, and (c) the balance being a bait base.

A third aspect of the present invention is a method of controlling insect pests, particularly cockroaches, by applying to areas to be controlled an effective amount of the above composition.

Finally, a fourth aspect of the present invention is a kit which can be used by the ultimate consumer at the site of application which contains the means for the preparation and application of the above-described composition, optionally in gel form, and includes (a) a closed impermeable container having a water-sensitive insecticide pellet or powder therein, and (b) a closed packet including a base bait including feeding stimulants and, optionally, one or more gelling agent(s). The kit may further include a means for dispensing the ready-to-use bait. Otherwise, the mixing packet may be used to apply the composition.

BRIEF DESCRIPTION OF THE DRAWING

The FIGURE is a chart comparing the mean knockdown time on applying an acephate gel versus a fipronil gel for cockroaches.

DETAILED DESCRIPTION OF THE INVENTION

The invention involves a water-based insecticidal bait composition which includes a water-sensitive insecticide, water and a bait base which includes feeding stimulants and, optionally, at least one or more gelling agents. The composition is preferably a gel and may be prepared at the site of application by the process described in detail below using a kit, if desired, as described below. The composition of the present invention has the advantages of being rapidly acting against the insect pests, particularly cockroaches, and can be applied easily to cracks, crevices and voids or other insect harborage areas.

Insecticide

A water-sensitive insecticide is one which is soluble in water but is also water degradable. Acephate is a preferred insecticide for the rapid acting, water-based composition of the present invention. Acephate is a fine crystalline powder that is water soluble. It is a desirable active ingredient because there is no known insecticide resistance and it has very low mammalian toxicity. Acephate has a molecular formula of $C_4H_{10}NO_3PS$ and is chemically known as O,S-dimethyl acetylphosphoramidothioate. Typically, acephate and other water-sensitive insecticides can be used in the composition at a minimum content of about 0.1 wt-%. The preferred range is a concentration of about 0.1 to about 5 wt-%. The most preferred amount of acephate in a gel composition is about 1 wt-%. Other water-sensitive insecticides include, for example, methamidophos, chemically known as O,S-dimethyl phosphoramidothioate, which is the deacetyl analog of acephate.

Water

As a water-based composition, water is an essential ingredient of the present invention and is used to dissolve the insecticide and soluble components within the bait base. The amount of water used may vary depending on the amount of insecticide and the amount of bait base. Thus the amount of water may range from 3 to 40 wt-% of the total composition. Preferably, water is used at about 22–32 wt-%. In a preferred embodiment, 30 wt-% of water is used in a 1.0 wt-% acephate composition.

Bait Base

The bait base includes a solid mixture of feeding stimulants and attractants which preferably includes at least one gelling agent. Feeding stimulants are included in the composition to attract the insect to the bait, and to entice the insect to eat the bait. Preferable feed stimulants include mixtures of carbohydrates and proteins. Examples of carbohydrates are maltodextrins and the like; carbohydrate complexes, corn syrup solids, sugars such as sucrose, glucose, fructose, starches such as corn, potato and the like. Examples of proteins include yeast extracts and milk solids, e.g. whole milk powder.

The feeding stimulants may include, if desired, a gelling agent serving a dual function such as, for example, starches. These starches are preferably modified, for example, a modified corn starch. Other gelling agents which may be used as part of the bait base include, for example, gums, e.g. xanthan gum; agars; agaroses; carageenans; bentonite; alginates; collagens; gelatin; polyacrylates; celluloses, cellulose derivatives; polyethylene glycols; polyethylene oxides; polyvinyl alcohols; dextrans; polyacrylamides; polysaccharides, or any other common gelling agent or viscosity enhancing agent. The preferred gelling agents for the present invention are modified starches.

In addition to feeding stimulants and gelling agents, the bait base may also contain additional attractants. Examples of attractants are odorants and flavorants such as, for example, cyclotenes and the like, plant extracts such as fenugreek and the like, alcohols such as ethanol, or a volatile ester in combination with ethanol. Said volatile ester is made from a combination of a $C_1$–$C_6$ branched or unbranched alcohol with $C_1$–$C_3$ carboxylic acid. Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof. Carboxylic acids useful in manufacturing the ester attractant of the invention include acetic acid, propionic acid, butyric acid, mixtures thereof, and others. The associated reactive analogs of the respective carboxylic acids can be used, for example, the acid chloride or acid anhydride. The preferred volatile ester for use is a lower alcohol acetate ester such as n-amyl acetate, isoamyl acetate, isobutyl acetate, n-propyl acetate, ethyl acetate or mixtures thereof. As with gelling agents and feeding stimulants, some of the ingredients may overlap in category as they can be both attractants and feeding stimulants, for example, the proteins mentioned above, odorants and flavorants.

The bait base may further include as part of the solid mixture up to 50 wt-% (of the total bait base) of borax or boric acid which can be used to lengthen the insecticidal activity of the composition.

The feeding stimulants, attractants and, optionally, gelling agents are the components of the bait base which contain the balance of the composition depending on the amount of insecticide and water employed to arrive at the composition. While the bait base containing feeding stimulants, optional gelling agents and other attractants contains the balance of the composition, the amount of gelling agent, when used, in this bait base may vary from about 0.1 to 5 wt-% of the total solid mixture. The preferred amount of gelling agent is about 1 wt-% of the solid bait base mixture.

Method of Preparation

The insect pest bait composition is designed to be prepared, if desired, at the site of use and may employ a kit which forms part of the present invention. The process is best described as follows:

1. The active ingredient is contained and stored in its technical form (95.0%–100% pure) within a glass or otherwise impermeable container prior to use. The water-sensitive insecticide is preferably contained in the form of a pellet or powder and the container preferably has a removable cover and is preferably a glass vial.

2. The bait is prepared by combining the insecticide with a specified amount of water diluent. The solution is agitated until the insecticide is completely dissolved.

3. The finished insecticide solution is then combined with a bait base which is a solid mixture of feeding stimulants, optional gelling agent and, if desired, other attractants. This mixture is thoroughly agitated and, if desired, allowed to gel.

The bait base is preferably contained in a packet, e.g., typically a resealable plastic bag. When the insecticide solution is added, the plastic bag is resealed and the contents mixed preferably by thoroughly kneading the materials. The mixed material can be poured into a dispensing means, e.g. a syringe or dispensing cartridge, or alternatively left in the original mixing packet, until ready for use. Typically, for a 1% acephate composition containing a gelling agent, the gelling time is approximately 20 minutes.

Depending on the amounts of active ingredient, feed stimulants and water, the composition may have a viscosity ranging from about 50,000 to about 1,500,000 centipoise. Typically, with a 1 wt-% acephate gel composition, and using 30% water and bait base as the balance, the viscosity of the resulting gel is about 180,000 centipoise.

Method of Use

Once the composition is formed, it can be applied directly onto cracks and crevices for the control of insect pests, particularly cockroaches.

Application of the composition is useful for food and feed handling establishments, such as restaurants; dairies; packaging, bottling and canning plants; bakeries; mills or anywhere food and feed is stored, prepared, processed and packaged.

The composition is also useful in spot and crack and crevice treatments in food areas. These include, for example, where food or feed is received, stored, prepared, served, packaged, handled in an enclosed system and where edible waste is stored. The bait composition may be directly applied into cracks and crevices, where equipment meets floors and walls; equipment and counter legs; bases, motors and conduits; holes and openings leading to wall voids where insects hide.

The composition may also be used in non-food areas of feed and food handling establishments including, for example, garbage rooms, restrooms, laboratories, offices, locker rooms, boiler and equipment rooms, garages, mop closets and storage. The composition also is applied to cracks and crevices around baseboards, around water and drain pipes, underneath and behind sinks, lockers, tables, and similar areas where insects may hide.

Finally, the composition may be employed in serving areas of food service establishments including, for example, dining rooms, mess halls and other areas where prepared food is served. The composition is applied in pea-sized or smaller placements onto selected surfaces such as baseboards, underneath booths and into cracks and crevices.

The Kit

Also part of the present invention is a kit which provides the necessary materials, containers and devices for the ultimate user to prepare the bait composition and apply it to the necessary areas including cracks and crevices. The kit is included as a one package option for the ultimate user of the bait composition.

As part of the kit, a container which is impermeable and has a cover for closing contains the water-sensitive insecticide in pellet or powder form. The container is preferably a glass vial.

The kit also includes a closed packet where the base bait solid mixture is contained. The closed packet is preferably a resealable plastic bag in which the materials are thoroughly mixed and/or kneaded after adding the insecticide aqueous solution.

Optionally, the third part of the kit includes a dispensing container which is also closable. The container is preferably a cartridge, syringe or cylinder which holds the combination of the aqueous insecticide solution thoroughly mixed with the bait base material. The dispensing container can be used for allowing the mixture to set and form a gel if desired. As an example, the dispensing cartridge is then placed in a bait applicator or connected to a bait applicator for application of the composition to the cracks and crevices.

The entire kit can be obtained as a unitary system assembled in a packet for use at the site.

The following examples are intended to illustrate the invention but are not to be construed in limiting.

EXAMPLES

Example 1

The following acephate composition was prepared:
7.0% bakers yeast extract (Universal Flavor Inc. CAS#8013-01-2)
19.0% sucrose (United Sugar Company. CAS#57-50-01)
9.0% ProMax 70L Soy Protein Concentrate (Central Soya, Code 4510.)
39.0% Calf's Milk Replacer (Cargill, Inc. CAS# N/A)
24.0% water
1.0% glycerol
1.0% acephate (Valent Corp. O,S-dimethyl acetylphosphoramidothioate)

The acephate was dissolved in water, shaken in a covered container and then added to the mixture of solid ingredients identified above. The ingredients were then allowed to set.

Example 2

The following test was carried out using the formulation of Example 1 to measure acephate degradation. The 1.0% acephate formulations of Example 1 were compared for efficacy against cockroach adults and nymphs with the jar/smear method described hereinafter. The 4-week aging (ambient) data are reported in the following table as KT50, wherein KT50 is the time in hours to kill 50% of the cockroach population.

TABLE

|  | Fresh | 1 wk | 2 wk | 4 wk |
| --- | --- | --- | --- | --- |
| Adult Males: |  |  |  |  |
| FB#10 | 0.685 | 1.035 | 1.157 | 1.532 |
| Adult Fmls: |  |  |  |  |
| FB#10 | 4.780 | 5.995 | 1.677 | 5.082 |
| Lrg Nmphs: |  |  |  |  |
| FB#10 | 1.217 | 6.325 | 1.187 | 4.587 |
| Sm Nmphs: |  |  |  |  |
| FB#10 | 0.298 | 2.134 | 1.622 | 4.998 |

All biological data indicate that the formulation remains effective against all life stages for 4.0 weeks after application.

The jar/smear method is described here:

Materials
1. Bait formulas for screening.
2. Mason jars coated on the upper lip with petrolatum to prevent escape.
3. Balance for measuring bait.
4. German cockroaches; 10 per jar.
5. Stop watch.

Method
1. Allowed 4 hours for cockroaches to acclimate with food and water in jars. Allowed alternative food and water to be present during testing period.
2. Applied 0.3 g of bait to one lip of an inverted plastic weigh boat (simulated crack & crevice treatment).
3. Following acclimation, ca, 4 hours, placed the baited (and inverted) weigh boat flatly into the jar. Repeated for all cockroach jars in sequence.
4. Measured the cockroach mortality over time and determined the KT50 for each cockroach life stage.

Example 3

The following formulation was prepared with the following ingredients:
1.0 wt-% acephate, 30 wt-% water, and 69 wt-% bait base of the following composition:

| Bait Base Composition | | |
| --- | --- | --- |
| Ingredients | Supplier | Wt % |
| Calf's Milk Replacer CAS # N/A | Cargill, Inc. Minneapolis, Minnesota 55440 | 71.31 |
| 6X powdered sugar CAS # 57-50-1 | United Sugar Company Moorhead, Minnesota 56561 | 5.40 |

-continued

Bait Base Composition

| Ingredients | Supplier | Wt % |
|---|---|---|
| bakers yeast extract CAS # 8013-01-2 | Universal Flavor Inc. Indianapolis, Indiana 46241 | 8.80 |
| food starch - modified CAS # 113894-92-1 | National Starch and Chemical Bridgewarer, New Jersey 08807 | 0.94 |
| sorbitol CAS # 50-70-4 | Archer Daniels Midland Decatur, Illinois 62526 | 3.70 |
| fructose CAS # 57-48-7 | A. E. Staley Manufacturing Co. Decatur, Illinois 62525 | 6.90 |
| sodium chloride CAS # 7647-14-5 | Cargill, Inc. Minneapolis, Minnesota 55440 | 1.25 |
| potassium sorbate CAS # 24634-61-5 | Archer Daniels Midland Decatur, Illinois 62526 | 0.38 |
| citric acid, anhydrous CAS # 77-92-9 | Archer Daniels Midland Decatur, Illinois 62526 | 1.32 |
| Total | | 100% |

1. The acephate-storage (vial) was opened and 30 ml of water was added to the acephate, 1.04 g). The vial cover was closed and the vial shaken until the acephate was completely dissolved.

2. The vial contents were then added to one packet of bait paste (described above), 68.9 g in a zip-lock bag. The packet was closed and thoroughly mixed by shaking and kneading.

3. The bait mixture was poured into a dispensing cartridge, covered and allowed to set for 20 minutes for the bait to gel. The resulting gel had a viscosity of about 180,000 centipoise.

Example 4

The gel composition of Example 3 was compared with regard to mean knockdown time of cockroaches as effected by the feeding time of the bait composition with a commercially available gel composition which contains fipronil as the active ingredient in a concentration of 0.01 %. The commercially available fipronil gel composition is used in the same manner as the composition of the present invention and is claimed to be rapid acting. The results of the tests are shown in FIG. 1. The longest mean knockdown time observed for the composition of the present invention was 1.62 hours in a 60-second feeding time. In contrast, the shortest fipronil mean knockdown time was 4.42 hours in the same feeding time, 60 seconds. Notably, in a 5-second feeding time, the gel composition of the present invention had a mean knockdown time of 1.18 hours whereas the fipronil gel took 20.28 hours for the same five second feeding time.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An insecticidal composition comprising:
   (a) about 0.1 wt. % to about 5 wt. %, based on the weight of the composition, of a water-sensitive insecticide comprising at least one of acephate or methamidophos;
   (b) about 22 wt. % to about 40 wt. %, based on the weight of the composition, of water to dissolve at least a part of the water-sensitive insecticide in the water;
   (c) bait base comprising at least one of an attractant or a feeding stimulant, and comprising up to 50 wt. %, based on the weight of the bait base, of borax or boric acid to lengthen the insecticidal activity of the composition, wherein the borax or boric acid is present in an amount sufficient to lengthen the insecticidal activity of the composition.

2. An insecticidal bait composition according to claim 1, wherein the water-sensitive insecticide comprises acephate.

3. An insecticidal bait composition according to claim 1, wherein the composition comprises about 22 wt. % to about 32 wt. % water, based on the weight of the composition.

4. An insecticidal bait composition according to claim 1, wherein the feeding stimulant comprises at least one of carbohydrates or proteins.

5. An insecticidal bait composition according to claim 1, wherein the feeding stimulant comprises at least one of maltodextrins, carbohydrate complexes, corn syrup solids, sugars, or starches.

6. An insecticidal bait composition according to claim 1, wherein the feeding stimulant comprise at least one of yeast extracts or milk solids.

7. An insecticidal bait composition according to claim 1, wherein the bait base comprises a gelling agent.

8. An insecticidal bait composition according to claim 7, wherein the bait base comprises at least one of xanthan gum, agars, agaroses, bentonite, alginates, collagens, gelatins, polyacrylates, celluloses, cellulose derivatives, polyethylene glycols, polyethylene oxides, polyvinyl alcohols, dextrans, polyacrylamides, polysaccharides, or modified starches.

9. An insecticidal bait composition according to claim 1, wherein the bait base comprises an attractant comprising at least one of an odorant or a flavorant.

10. An insecticidal bait composition according to claim 1, wherein the composition comprises about 0.1 wt. % to about 5 wt. % gelling agent, based on the weight of the base bait.

11. An insecticidal bait composition according to claim 1, wherein the composition has a viscosity ranging from about 50,000 cps to about 1,500,000 cps.

* * * * *